United States Patent [19]
Haley et al.

[11] Patent Number: 5,693,764
[45] Date of Patent: Dec. 2, 1997

[54] NUCLEOTIDE OR NUCLEOSIDE PHOTOAFFINITY COMPOUND MODIFIED ANTIBODIES, METHODS FOR THEIR MANUFACTURE AND USE THEREOF AS DIAGNOSTICS AND THERAPEUTICS

[75] Inventors: Boyd E. Haley, Nicholasville; Heinz Kohler, Lexington; Krishnan Rajagopalan, Lexington; Gabriela Pavlinkova, Lexington, all of Ky.

[73] Assignee: The University of Kentucky Research Foundation, Lexington, Ky.

[21] Appl. No.: 634,225

[22] Filed: Apr. 18, 1996

Related U.S. Application Data

[62] Division of Ser. No. 208,822, Mar. 11, 1994, Pat. No. 5,596,081.

[51] Int. Cl.$^6$ .............................. C07K 16/00; C12P 21/00
[52] U.S. Cl. .............................. 530/391.1; 530/391.3; 530/391.5; 530/391.7; 530/391.9; 436/547
[58] Field of Search .................. 530/391.1, 391.5, 530/391.7, 391.9, 391.3; 436/547

[56] References Cited

U.S. PATENT DOCUMENTS

| | | | |
|---|---|---|---|
| 4,861,579 | 8/1989 | Meyer et al. | 424/9 |
| 5,045,451 | 9/1991 | Uhr et al. | 435/7.23 |
| 5,106,951 | 4/1992 | Morgan et al. | 530/391.9 |
| 5,272,055 | 12/1993 | Haley | 435/6 |

OTHER PUBLICATIONS

Harris et al., *Tibtech*, vol. 11, pp. 42–44 (1993).
Bach, et al., *Immunology Today*, vol. 14, No. 9, pp. 421–425, 1993.
Waldmann, *Science*, vol. 252, pp. 1657–1662, 1991.
Seaver, Genetic Engineering News, pp. 10 & 21, 1994.
Canevari, et al., *Annals of Oncology*, vol. 5, pp. 698–701, 1994.
Stein, et al., *Science*, vol. 261, pp. 1004–1012 1993.
Borrebaeck, *J. of Immunol. Methods*, vol. 123, pp. 157–165, 1989.
Spalding, *Bio/Technology*, vol. 11, pp. 428–429, 1993.

*Primary Examiner*—Toni R. Scheiner
*Attorney, Agent, or Firm*—Burns, Doane, Swecker & Mathis, L.L.P.

[57] ABSTRACT

Sites on antibodies having affinity for photoaffinity compounds, in particular purine or azidopurine containing compounds are taught. These sites provide for the site-specific attachment of nucleotide photoaffinity compounds to antibodies, e.g., ATP- or GTP-analog photoaffinity compounds by photochemical means. These nucleotide photoaffinity compounds may additionally be attached to molecules having a desired therapeutic or diagnostic activity, and the resultant conjugates used as diagnostics or therapeutics.

15 Claims, 5 Drawing Sheets

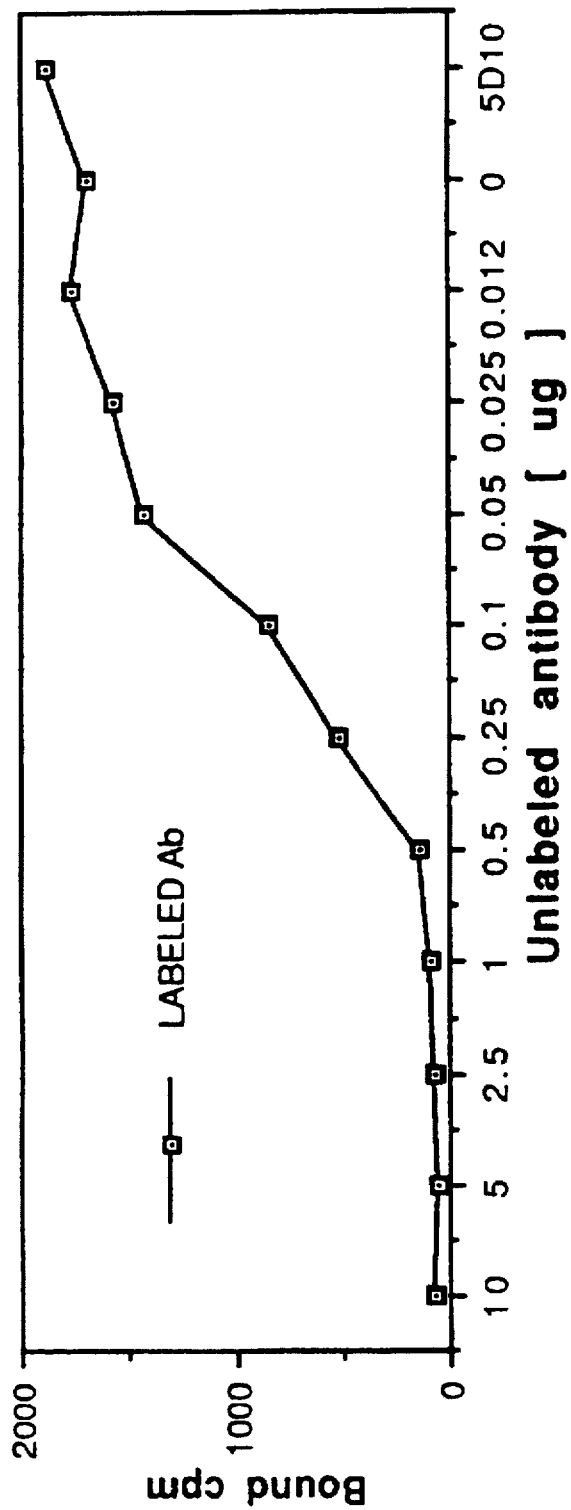

Figure 4: An antibody competion assay for the photolabeled antibody. Idiotype antibody was used as antigen for plate coating (500ng/well). Same amount labeled 3H1(3μg) was mixed with the indicated amount of the unlabeled antibody and incubated for 2 h at 25ºC. At termination of the experiment the wells were washed, dried, cut and counted by liquid scintillation. 5D10 was used as non-specific cold inhibitor.

NUCLEOTIDE OR NUCLEOSIDE PHOTOAFFINITY COMPOUND MODIFIED ANTIBODIES, METHODS FOR THEIR MANUFACTURE AND USE THEREOF AS DIAGNOSTICS AND THERAPEUTICS

This application is a divisional, of Application Ser. No. 08/208,822 filed Mar. 11, 1994 now U.S. Pat. No. 5,596,081.

CROSS REFERENCE TO RELATED APPLICANTS

This application relates to U.S. Ser. No. 08/138,109 filed on Oct. 20, 1993. This application is incorporated by reference in is its entirety herein.

FIELD OF THE INVENTION

The present invention relates to the discovery of novel site or sites on antibodies having high affinity for nucleotide or nucleoside photoaffinity compounds. The present invention further relates to the use of these novel site or sites as a target for photoaffinity labeling using nucleotide or nucleoside photoaffinity compounds and for the attachment of molecules having a particular chemical or biological activity. In particular, the present invention concerns a site or sites on antibodies having high affinity for purine or purine derivative containing photoaffinity compounds, e.g., ATP- or GTP-analog photoaffinity compounds and the use of these sites as targets for purine or purine derivative photoaffinity compounds or other heterocyclic base containing compounds which have affinity for these sites and for the attachment of molecules having a particular chemical or biological activity.

The present invention further relates to compositions, methods, and test kits which contain or use the subject nucleotide photoaffinity labeled antibodies. The present invention still further relates to novel compositions, methods and test kits which use the procedure of photoaffinity labeling with nucleotide affinity probes, to attach molecules having a desired chemical or biological activity to antibody molecules.

BACKGROUND OF THE INVENTION

Antibodies are specific immunoglobulin molecules produced by vertebrate immune systems in response to challenge by foreign proteins, glycoproteins, cells, or other typically foreign substances. The sequence of events which permits an organism to overcome invasion by foreign cells or to rid the system of foreign substances is at least partially understood. An important part of this process is the manufacture of antibodies which bind specifically to a particular foreign antigenic substance. The binding specificity of such polypeptides to a particular antigen is highly refined, and the multitude of specificities capable of being generated by an individual vertebrate is remarkable in its complexity and variability. Thousands of antigens are capable of eliciting antibody responses, each almost exclusively directed to the particular antigen which elicited it.

Immunoglobulins include both antibodies, as above described, and analogous protein substances which lack antigen specificity. The latter are produced at low levels by the lymph system and in increased levels by myelomas.

Antibodies are produced by B lymphocytes and represent the humoral arm of the immune defense system. Because of their antigen specificity, antibodies comprise numerous diagnostic and therapeutic applications. For example, they can be used as specific immunoprecipitating agents to detect the presence of an antigen which they specifically bind by coupling the antigen-antibody reaction with suitable detection techniques such as labeling with radioisotopes or with detectable enzymes (RIA, EMIT, and ELISA). Antibodies are thus the foundation of immunodiagnostic tests for many antigenic substances.

Another important application of antibodies involves their use as therapeutics. The therapeutic administration of antibodies has recently been described for the treatment of numerous disease conditions including cancer, and numerous infectious diseases.

The therapeutic usage of antibodies has been the focus of greater interest since the development of monoclonal antibody/hybridoma technology by Kohler and Milstein (*Proc. Natl. Acad. Sci. USA*, 77:2197 (1980)). Monoclonal antibodies, which are produced by hybridomas, are preferable to polyclonal antibodies because of their greater antigenic specificity. Monoclonal antibodies have a lesser tendency than polyclonal antibodies to non-specifically bind to non-targeted moieties, e.g., cells which do not express the corresponding antigen. However, monoclonal antibodies still suffer from some disadvantages, e.g., they tend to be contaminated with other proteins and cellular materials of hybridoma (mammalian) origin. Also, hybridoma cell lines tend to be unstable and may alter the production of the antibody produced or stop secreting the antibody altogether.

In an effort to obviate some of the problems associated with polyclonal and monoclonal antibodies, and further to obtain a reproducible supply of antibodies having a defined binding specificity, researchers have used recombinant techniques to produce immunoglobulins which are analogous or modified in comparison to antibodies normally found in vertebrate systems. For example, U.S. Pat. No. 4,816,397 issued on Mar. 28, 1989 to Boss et al. and U.S. Pat. No. 4,816,567 issued on Mar. 28, 1989 to Cabilly et al. disclose recombinant immunoglobulins and immunoglobulin fragments, and methods for their production.

To enhance or modify the properties of recombinant antibodies, it is further known to produce mutant or chimeric antibodies, e.g., which comprise sequences from several different mammalian species or bispecific antibodies which comprise antigenic binding sequences from two different antibodies. For example, humanized antibodies which comprise antigen-binding sites from a non-human species (typically murine) but wherein the remainder of the immunoglobulin is of human origin are known in the art, and have been reported to have significant potential as therapeutics because of their reduced antigenicity. It is further known to produce recombinant antibodies of single chain form, which completely lack constant domain sequences but which bind antigen. (See, Bird et al., *Science*, 242, 423–426 (1988)).

In order to increase the efficacy of antibody molecules as diagnostic or therapeutic agents, it is conventional to covalently bind or complex desired molecules thereto, in particular effector or reporter molecules. Effector molecules essentially comprise molecules having a desired activity, e.g., cytotoxic activity. By contrast, a reporter molecule is defined as any moiety which may be detected using an assay. Examples of effector molecules which have been attached to antibodies include by way of example, toxins, anti-tumor gents, therapeutic enzymes, radionuclides, antiviral agents, chelating agents, cytokines, growth factors, and polynucleotides. Examples of reporter molecules which have been conjugated to antibodies include, by way of example, enzymes, radiolabels, fluorescent labels, phosphorescent molecules, chemiluminescent molecules, chromophores, luminescent molecules, and colored particles.

While it is desirable to attach molecules to antibodies in order to impart a desired activity to the antibody or provide for the detection thereof, the attachment of desired molecules to antibodies is not always possible to carry out conveniently, or effectively, because such attachment may result in loss of antibody activity. In particular, current methods for generating radiolabeled antibodies for diagnostic and therapeutic use suffer from such limitations. For example, the ratio of target-specific versus non-specific uptake of radiolabeled antibodies used in tumor imaging is often low, resulting in unclear images or missing tumor sites. Moreover, the low therapeutic index of radiolabeled antibodies limits the use of high radiation doses in radiation therapy.

The underlying reason for such problems is largely because the labeling chemistry for introduction of the radiolabel results in the partial denaturation of the antibody structure, which in turn causes the antibodies to aggregate in vivo or in vitro. Aggregated and damaged immunoglobulins are recognized by scavenger cells in the body, such as macrophages and Kupffer cells in the liver and lung.

Another problem is that most coupling strategies result in non site-specific attachment of the molecule to the antibody molecule, in particular, attachment may occur at antibody residues which are essential for antigen binding or other antibody functions. For instance, a known site of attachment of desired molecules to antibody molecules comprise thiol groups, since thiol groups occur naturally in proteins as cysteine residues. However, such residues are relatively uncommon, are often inside the molecule and are frequently involved in forming disulfide bridges within or between protein molecules. Thus, there is a danger that if a naturally occurring cysteine residue is used as a site of attachment, it will interfere with the normal folding and stabilization of the antibody protein.

In an effort to obviate such problems, alternative strategies have been developed which provide for site-selective attachment of a desired molecules to antibodies, without loss of antigen-binding activity. For example, it is known to produce recombinant antibodies comprising cysteine residues introduced into their surface structure to provide a thiol group which is available for covalent binding to an effector or reporter molecule. This method has been reported to facilitate the site-specific attachment of desired molecules without loss of antigen binding properties. (See, U.S. Pat. No. 5,219,996 issued on Jun. 15, 1993 to Bodmer et al.) However, this is not always possible or convenient since it obviously requires the possession of a recombinant DNA encoding the particular antibody.

It has further been proposed to derivatize immunoglobulins by selectively introducing sulfhydryl groups in the Fc region of an immunoglobulin, using reaction conditions which purportedly do not result in alteration of the antibody combining site. Antibody conjugates produced according to this methodology are disclosed to exhibit improved longevity, specificity and sensitivity (U.S. Pat. No. 5,196, 066 issued on Mar. 2, 1993 to Bieniarz et al.).

Site-specific attachment of effector or reporter molecules, wherein the reporter or effector molecule is conjugated to a carbohydrate residue in the Fc region has also been disclosed in the literature. (See, e.g., O'Shannessy et al., *J. Immun. Meth.*, 99, 153–161 (1987)). This approach has been reported to produce diagnostically and therapeutically promising antibodies which are currently in clinical evaluation.

Another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this is disadvantageous since it results in loss of antigen binding by the antibody conjugate.

Thus, based on the foregoing, it is clear that there still exists a significant need in the an for improved methods of attaching molecules to antibodies, in particular effector or reporter molecules, which are site-specific and which moreover result in antibody conjugates having substantially unaltered structure and biological activity, most especially antigen binding activity.

Molecules containing azido groups have been shown to form covalent bonds to proteins through reactive nitrene intermediates, generated by low intensity ultraviolet light. Potter & Haley, *Meth. in Enzymol.*, 91,613–633 (1983). In particular, 2- and 8- azido analogues of purine nucleotides have been used as site directed photoprobes to identify nucleotide binding proteins in crude cell extracts. Owens & Haley, *J. Biol. Chem.*, 259:14843–14848 (1987); Atherton et al., *Biol. of Reproduction*, 32, 155–171 (1985). The 2- and 8-azido nucleotides have also been used to map nucleotide binding domains of purified proteins. Khatoon et al., *Ann. of Neurology*, 26, 210–219 (1989); King et al., *J. Biol. Chem.*, 269, 10210–10218 (1989); and Dholakia et al., *J. Biol. Chem.*, 264, 20638–20642 (1989).

Photoaffinity probes have been used to determine specific nucleotide binding sites on a biologically active recombinant peptide molecule. Campbell et al., PNAS, 87, 1243–1246 (1990). The probes have also been used to study enzyme kinetics of purified proteins. Kim et al., *J. Biol. Chem.*, 265, 3636–3641 (1990).

Recently, ATP or GTP analog photoaffinity labeled probes have been used to detect a glutamine synthetase nucleotide binding protein having an apparent molecular weight of about 42,000 proteins to aid in the diagnosis of Alzheimer's disease in a mammal. U.S. Ser. No. 08/138,109 filed on Oct. 20, 1993 by Haley et al. Additionally, ATP or GTP analog photoaffinity-labeling reagents have been disclosed for use in the detection of particular nucleotide binding proteins to aid in the diagnosis of cancer in a mammal and in the diagnosis of leukemia in a mammal. (Id.)

However, while it had been previously known to use nucleotide photoaffinity probes, and specifically purine containing photoaffinity analogs (GTP- and ATP-analogs), to map nucleotide binding domains of purified proteins and to identify specific nucleotide binding sites on recombinant peptide molecules, the use of nucleotide photoaffinity probes to label antibodies has not been previously reported in the literature. This is essentially because it had not been previously known that antibody molecules comprise nucleotide photoaffinity sites, and in particular, sites having high affinity for purine, azidopurine and other similar heterocyclic bases, which may be efficiently photolabeled using appropriate photoaffinity probes.

OBJECTS AND SUMMARY OF THE INVENTION

It is, therefore, an object of this invention to identify nucleotide or nucleoside affinity sites on antibodies which provides for the site specific photoinsertion of desired molecules to antibodies. It is further a specific object of the invention to characterize the effects of these affinity sites on antibody function.

It is a more specific object of this invention to identify a site or sites on antibodies having high affinity for purines, azido-purines and other similar heterocyclic organic compounds, in particular ATP- or GTP-analog photoaffinity compounds.

It is another specific object of the invention to provide methods for coupling desired molecules, e.g., effector or reporter molecules to an antibody by site-specific attachment of the molecules to nucleotide affinity site or sites contained on the antibody molecule or by attachment of the molecules to a nucleotide photoaffinity compound which has been photoinserted at said nucleotide affinity site.

It is a more specific object of the invention to provide methods for site-specifically photoaffinity coupling a purine, azidopurine or similar heterocyclic base containing compound, in particular an ATP- GTP-analog photoaffinity compound, which compound is attached to one or more molecules having a desired activity, to a site or sites contained on the antibody molecule having high affinity for purine, azidopurine or other similar heterocyclic bases, or to preferably an ATP- or GTP-analog photoaffinity compound, which as been photoinserted onto said site or sites.

It is another object of the invention to provide antibodies conjugated to desired molecules, in particular, effector or reporter molecules wherein such molecules are site-specifically attached to the antibody via a nucleotide affinity site, or to a nucleotide photoaffinity analog attached to said site.

It is a more specific object of the invention to provide antibodies conjugated to desired molecules, in particular, reporter or effector moieties wherein such ligands are attached to the antibody at a site having high affinity for purine, azidopurine and other similar heterocyclic bases, in particular ATP- or GTP-analog photoaffinity compounds, or to a nucleotide photoaffinity compound attached to said site.

It is another object of the invention to provide a method for photoaffinity labeling of antibodies by the attachment of nucleotide photoaffinity probes to a nucleotide affinity site or sites contained on the immunoglobulin molecule. It is a more specific object of the invention to provide a method for photoaffinity labeling of antibodies by the attachment of a labeled purine, azidopurine or other similar heterocyclic base containing photoaffinity probe, and in particular an ATP- or GTP-analog photoaffinity labeled compound to a site or sites on the antibody having high affinity of purine, azidopurine and/or similar heterocyclic bases, and in particular ATP- or GTP-analog photoaffinity compounds.

It is another objeat of the invention to provide photoaffinity labeled antibodies and compositions containing, wherein such antibodies have been coupled to a nucleotide photoaffinity probe via a nucleotide affinity site contained on the antibody molecule.

It is a more specific object of the invention to provide photoaffinity labeled antibodies and compositions containing, wherein such antibodies have been coupled to a labeled purine, azidopurine and/or similar heterocyclic base containing photoaffinity probe, in particular a labeled ATP- or GTP-analog photoaffinity compound, at a site or sites on the antibodies having high affinity for purine, azidopurine and/or heterocyclic bases.

It is another object of the invention to provide improved methods of immunodetection of an antigen, wherein such methods include the detection and/or quantification of antigen-antibody complexes using a labeled antibody wherein the improvement comprises using as the labeled antibody a nucleotide or nucleoside photoaffinity compound labeled antibody, in particular a labeled purine or purine derivative containing compound labeled antibody, and more particularly a labeled ATP- or GTP-analog photoaffinity compound antibody.

It is another object of the invention to provide improved immunotherapeutics, wherein such immunotherapeutics comprise an antibody conjugated or complexed to molecules having therapeutic or cytotoxic activity, wherein the improvement comprises using as the immunoconjugate an antibody which comprises one or more therapeutic or cytotoxic molecules site-specifically attached to the antibody via a nucleotide or nucleoside affinity site on the antibody. In the preferred embodiment, the affinity site will have high affinity for purine derivatives, in particular ATP- or GTP-analog photoaffinity compounds. The present invention further provides methods of using said immunotherapeutics to treat various disease conditions, and as imaging agents.

It is another object of the invention to provide test kits for detection of antigens comprising diagnostically effective mounts of one or more of the following: antibodies, nucleotide photoaffinity probe, preferably an ATP- or GTP-analog photoaffinity compound, reporter, any substrate(s) necessary for the detection of the particular reporter, and diagnostic carriers, and wherein the various moieties may be separate from one another or may be in various forms of attachment.

It is a more specific object of the invention to provide test kits for detection of antigens comprising diagnostically effective mounts of one or more of the following: antibodies, a purine, azidopurine and/or a similar heterocyclic base containing photoaffinity probe, reporter, any substrates necessary for the detection of the reporter and diagnostic carriers, wherein the various moieties may be separate or may be in various forms of attachment.

It is yet another specific object of the invention to attach heavy metals to antibodies which may or may not be radioactive, in particular, triphosphate chelated heavy metals such as $^{111}In^{3+}$ by reacting said chelated heavy metals with nucleotide photoaffinity compounds before or after such nucleotide photoaffinity compounds are attached to a nucleotide affinity site or sites contained in an antibody molecule. Other suitable heavy metals for photoattachment include, e.g., mercury and iron. In the preferred embodiment, the nucleotide photoaffinity compound will comprise a purine, azidopurine and/or a similar heterocyclic base containing compound, and most preferably will comprise ATP- or GTP-analog photoaffinity compounds.

It is yet another specific object of the invention to provide a novel method of attaching nucleic acids to antibodies, e.g., antisense nucleic acids, DNA, RNA or mixtures thereof, comprising attaching said nucleic acids to the antibody molecule using a nucleotide affinity compound, preferably a purine, azidopurine or similar heterocyclic base containing nucleotide affinity compound, more particularly an ATP- or GTP-analog photoaffinity compound which comprises a highly negatively charged phosphate (tri or tetraphosphate) having high affinity for positively charged polylysine.

It is a more specific object of the invention to attach desired molecules, e.g., reporter, or effector molecules which contain one or more reactive amino groups, or which have been attached to a spacer comprising one or more reactive amino groups, to an antibody by reacting same with a nucleotide affinity compound having a reactive cis-hydroyl group containing ribose moiety, which cis-hydroyl group may be convened to a dialdehyde under gentle conditions, and wherein such attachment may be effected before or after the nucleotide affinity probe is attached to an antibody via nucleotide affinity site or sites contained on the antibody.

BRIEF DESCRIPTION OF THE FIGURES

FIG. 4 is a graph of the results of a solid phase binding assay [ELISA] which compares the ability of different amounts of unlabeled 3H1 monoclonal antibody (ranging from 0 to 10 µM) to inhibit binding of the same amount of [γ$^{32}$P]-8-N$_3$ATP labeled 3H1 monoclonal antibody to the corresponding idiotypic antibody, and wherein the 5D10 antibody is used as a non-specific cold (unlabeled) inhibitor. Photoincorporation is again quantified by liquid scintillation counting. The results show that cold (unlabeled) 3H1 monoclonal antibody inhibits binding of the labeled 3H1 antibody.

DETAILED DESCRIPTION OF THE PREFERRED EMBODIMENTS OF THE INVENTION

Figure 1:
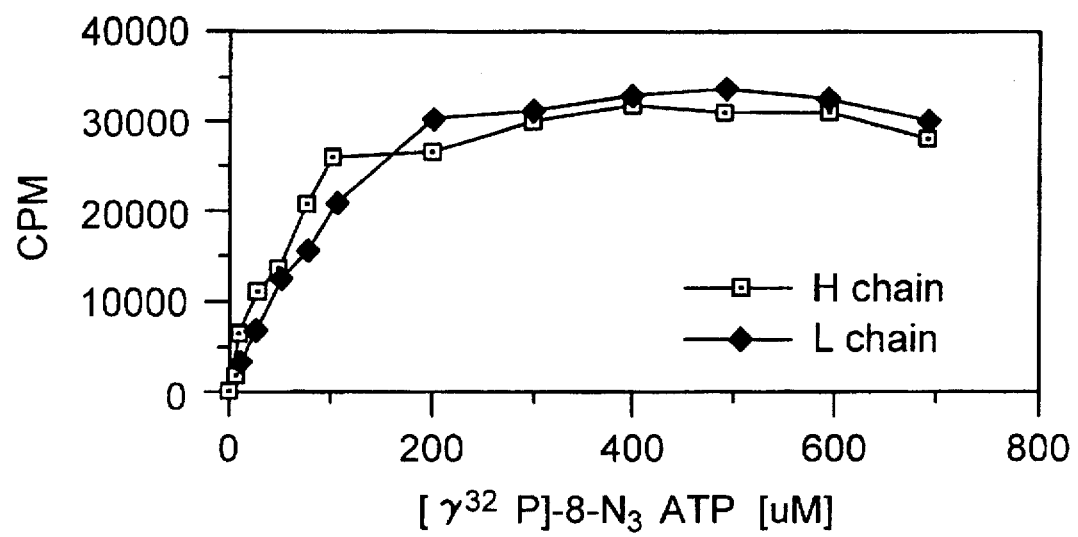
FIG. 1 is a graph which compares the photoincorporation of [γ$^{32}$P]-8-N$_3$ATP into the heavy and light chains of the SIC5 monoclonal antibody wherein the extent of photoincorporation is quantified by liquid scintillation counting. The results show that the radioactive probe covalently attached to both heavy and light chains.

The present invention provides the discovery that some, if not all, antibodies contain one or more photoaffinity sites which provide for the selective site-specific attachment of photoaffinity compounds thereto. In particular, it has been discovered that antibodies comprise one or more sites having high affinity for purines, azido-purines and other similar heterocyclic organic compounds, and specifically ATP- or GTP-analogs. However, the present inventors do not wish to be limited to purine or azidopurine binding sites, since, given the teachings in this application, other photoaffinity binding sites may further be identified, e.g., by reaction of antibodies with non-purine containing photoaffinity compounds, e.g., pyrimidine derivatives such as photoactive analogs of dUTP, including 5-azido-2'-deoxyuridine 5'-triphosphate (5 -N$_3$dUTP).

The purine or azidopurine nucleotide affinity site will hereinafter be referred to as the "purine ring binding" or simply the "PRB" domain or site.

The PRB site on antibody molecules was discovered after it was found by the present inventors that photoaffinity compounds, in particular purine or azidopurine photoaffinity compounds readily attach to antibodies and antibody fragments by a photoactivated chemical reaction which occurs under mild, physiological conditions. Specifically, it has been discovered that antibodies comprise one or more PRB sites which exhibit such a high affinity for purines and azidopurine photoaffinity analogs, that reaction of antibodies with purine and azidopurine photoaffinity analogs under mild, physiological conditions, and more particularly after only a single 2–5 minute photolysis results in nearly 100% photoattachment.

This is in contrast to the harsh and potentially damaging conditions which are generally required to facilitate the effective covalent attachment of desired molecules to antibodies. Thus, the present invention provides an improved method for the attachment of desired molecules to antibodies, since it utilizes reaction conditions which are more compatible with the preservation of labile biological molecules and living cells.

However, it should be emphasized that while the conditions which facilitate the attachment of nucleotide photoaffinity compounds to antibodies are inherently gentle, this, in itself, did not ensure a successful outcome. Foremost, prior to the invention, it could not have been predicted with any degree of certainty that this photoaffinity reaction would occur under any conditions, because it was not known that antibodies comprise site or sites having affinity for photoaffinity compounds, in particular nucleotide and nucleoside photoaffinity compounds, and more particularly sites having high affinity for purine, azidopurine or similar heterocyclic base containing photoaffinity compounds. Moreover, even assuming that the existence such sites had been known, it could not have been predicted that reaction with such sites with compatible photoaffinity compounds would not have adversely affected antibody activity, most especially the ability of the antibody to bind antigen. For example, it was entirely possible that the nucleotide or nucleoside photoaffinity compounds could have inserted in the antibody molecule at a site or sites within or sufficiently proximate to the antigen combining site, such that antigen binding activity was lost or substantially impaired. Alternatively, it was possible that the insertion of the nucleotide or nucleoside photoaffinity compounds into antibody molecules could have induced conformational changes in the antibody molecule causing substantial reduction or loss of other antibody functions. However, quite surprisingly it has been found that nucleotide photoaffinity analogs readily attach to antibodies, in a site-specific manner, under conditions which do not result in substantial loss of antigen binding activity.

Thus, the invention in general provides a novel means for site-specifically photoattaching desired molecules to antibodies nucleotide or nucleoside affinity sites contained in the antibody. The invention further provides general methods for studying the function of these nucleotide and nucleoside affinity sites, by binding different nucleotide and nucleoside photoaffinity compounds to these sites and evaluating their effects on antibody functions, e.g., effector functions.

As discussed in the Background of the Invention, methods for photoinsertion of nucleotide photoaffinity compounds, and specifically purine and purine analog photoaffinity compounds in proteins having specific nucleotide binding sites have been reported in the literature. The subject invention embraces any set of reaction conditions which provides for the effective photoinsertion of a nucleotide or nucleoside photoaffinity compound, preferably a purine, azidopurine or similar heterocyclic base containing photoaffinity analog, and most preferably an ATP- or GTP-analog photoaffinity compound, into an antibody molecule, which does not result in substantial loss of antigen binding.

Suitable methods for attaching nucleotide photoaffinity analogs to proteins are described, e.g., in Potter & Haley, *Meth. in Enzymol.*, 91:613–633, (1983); Owens & Haley, *J. Biol. Chem.*, 259:14843–148 48, (1987); Atherton et al, *Biol. of Reprod.*, 32:155–171, (1985); Khatoon et al, *Ann. of Neurology*, 26:210–219, (1989); King et al, *J. Biol. Chem.*, 269:10210–10218, (1989); Dholakia et al, *J. Biol. Chem.*, 264:20638–20642, (1989); Campbell et al, *Proc. Natl. Acad. Sci.*, 87:1243–1246, (1990); and Kim et al, *J. Biol. Chem.*, 265:3636–3641, (1990), which references are incorporated by reference in their entirety herein.

Any antibody or antibody containing composition which effectively binds nucleotide or nucleoside photoaffinity compounds is within the scope of the present invention. This includes by way of example, polyclonal and monoclonal antibodies, recombinant antibodies, chimeric antibodies, bispecific antibodies, single chain antibodies, antibodies from different species (e.g., mouse, goat, rabbit, human, rat, bovine, etc.), anti-idiotypic antibodies, antibodies of different isotype (IgG, IgM, IgE, IgA, etc.), as well as fragments and derivatives thereof. (e.g., (Fab)$_2$ fragments.)

Optimal reaction conditions will vary dependent upon factors including the concentration of antibodies in the particular composition, the isotype and/or species origin of such antibodies, and the number and affinity of nucleotide or nucleoside binding sites present on the particular antibodies. Suitable conditions can readily be determined by the skilled artisan by reference to the above-cited publications relating to nucleotide photoaffinity labeling of proteins, and the examples therein.

The invention further embraces the use of any nucleotide or nucleoside photoaffinity compounds which effectively photoinserts into one or more nucleotide affinity sites of a selected antibody under conditions which provide for the substantial retention of antigen binding activity. Moreover, if the antibody is to be used as a therapeutic agent, such conditions should preferably preserve other antibody functions, e.g., effector functions, comprised in the Fc portion of the antibody molecule (e.g., complement activation).

The particular nucleotide or nucleoside photoaffinity compound may be directly reacted with an antibody, or it may first be attached to another compound, e.g., a molecule having a desired effector function or a reporter molecule, e.g., a radioactive label.

Many nucleotide photoaffinity probes may be synthesized and used successfully. The photoaffinity compounds of the invention will preferably comprise adenine analogs, although guanine analogs can be substituted therefor. For example, purine binding sites may be effectively labeled by the following, and their 5'-mono-, di- and triphosphates: oligomers of a single azidoadenylyl species, such as, for example: 2-azido or 2-azidoadenylyl(2'-5')2-azidoadenylyl (2'-5')2-azidoadenosine; 2-azido or 8-azidoadadenosine; 8-azidoadenylyl(2'-5')-8-azidoadenylyl(2'-5')8-azidoadenosine; 8-azidoadenylyl(2'-5')- 8-azidoadenylyl(2'-5')8-azidoadenylyl-(2'-5')8-azidoadenosine; 2,8-diazidoadenylyl(2'-5')2,8-diazidoadenylyl(2'-5')2,8-diazido-adenosine; 2,8-diazidoadenylyl(2'-5')2,8-diazidoadenylyl (2'-5')-2,8-diazidoadenylyl(2'-5')2,8-diazidoadenosine; also oligomers of AMP and a single azidoadenylyl species, such as, for example: 2-azidoadenylyl(2'-5')2-(2'-5')adenosine; adenylyl(2'-5')8-azido adenyl(2'-5')8-azidoadenosine; also oligomers containing more than one azidoadenylyl species, such as, for example: 2-azidoadenylyl(2'-5')8-azidoadenylyl (2'-5')2-azidoadenosine; also oligomers resulting from any combination of the monomers AMP, 2-azido-AMP, 8-azido-AMP and/or 2,8-diazido-AMP, provided that at least one such monomer incorporated into the oligomer is an azido-AMP species.

In addition photoaffinity compounds of the invention may also include photoactive coenzyme analogs of NAD$^+$, exemplified by nicotinamide 2-azidoadenosine dinucleotide (2-azido-NAD+), or analogs of NADH, exemplified by nicotinamide 2-hydrazidoadenosine dinucleotide (2-azido-NADH).

Alternatively, guanine moieties can be defined in each of the exemplary compounds in place of the respective adenine moieties. Therefore, certain most preferred compounds of the present invention are synthesized from azidoguanosine 5'-triphosphates or combinations thereof, or from azidoguanosine 5'-triphosphates and ATP. The latter provides a (2'-5')oligomer containing both guanylyl and azidoguanylyl moieties.

Furthermore, photoaffinity compounds of the present invention may also include, for example, pyrimidine derivatives. For instance, photoactive analogs of dUTP, such as 5-azido-2'-deoxyuridine 5'-triphosphate (5-N$_3$dUTP), may be synthesized from dUMP and provide a pathway for the synthesis of other useful 5-substituted uridine nucleotides. The 5-diazouridine nucleotides may, for example, serve as active-site-directed photoaffinity probes or as substrates for polymerizing enzymes to generate additional photoactive nucleic acids which remain stable to extremes of pH and which remain effective photolabeling reagents in the presence of reducing agents. Moreover, since the synthesis of 5-N$_3$dUTP employs mild conditions, it is also possible to synthesize homopolymers of 5-N$_3$dUTP to provide single-stranded photoactive DNA of defined length. Using 5N$_3$UTP one can similarly produce photoactive RNA.

Generalized methods for the synthesis of aryl azides include nucleophilic displacement of a bromine, chlorine or nitro group by an azide ion or the addition of sodium azide to an acidic solution containing a diazotized primary aromatic amine.

To date the most widely used 8-azidopurine is probably 8N$_3$cAMP. One of the advantages of 8N$_3$cAMP is that in mammalian systems there are only two types of proteins that are known to bind cAMP with high affinity, the cAMP phosphodiesterases and the regulatory subunits of the cAMP-dependent protein kinases. The photoprobes [$^{32}$P]8N$_3$cAMP and [$^{32}$P]8N$_3$ATP have been employed to study, for example, the mechanisms of action of cAMP-dependent protein kinase. Photoactive analogs of GTP, e.g., [$^{32}$P] 8N$_3$GTP, have been developed to study, for example, tubulin polymerization, while photoactive analogs of UTP, e.g., [$^{32}$P]5N$_3$dUTP have been generated to study, for example, the binding site of DNA binding proteins.

Preferred compounds of the present invention are synthesized from azidoadenosine 5'-triphosphates or combinations thereof, which provide a (2'-5')oligomer containing both adenylyl and azidoadenylyl moieties. Especially preferred photoaffinity compounds for use in the present invention include in particular 2-azido-ATP, 8-azido-ATP and benzophenone-ATP or other compounds which effectively compete with 2 or 8-azido-ATP for occupancy of the PRB binding domain.

As noted, these photoaffinity compounds may further be attached to other molecules, e.g., effector molecules or reporter molecules, provided that such molecules do not adversely affect the ability of the photoaffinity compound to effectively photoinsert into nucleotide binding site or sites contained in the particular antibody, or provided that such molecules may be effectively attached to a nucleotide or nucleoside photoaffinity compound which has been bound to the particular antibody.

Nonradioactive reporter molecules or labels can be divided into two categories: (i) chromogenic, fluorogenic, or chemiluminescent dyes or (ii) ligands. Dyes are normally of from 8 to 40 carbon atoms, preferably from 9 to 30 carbon atoms. The dyes further normally contain from 1 to 10 heteroatoms usually oxygen, nitrogen, or sulfur, and normally contain no halogen atoms or up to 10 halogen atoms usually iodine, bromine, chlorine, or fluorine.

Chromogenic dyes may include phenol sulfonephthalein and analogs of tetrazolium.

Fluorogenic dyes may include fluorescein isothiocyanate, dichlorotriazinylamino fluorescein, morpholinorhodamine isothiocyanate, tetramethylrhodamine isothiocyanate, and 4-acetamido4-isothiocyanostilbene-2 with 2'-disulfonic acid. Fluorescent purine derivatives may also include, for example, the fluorescent GTP analog 2'3'-O-(2,4,6-trinitrocyclohexadienylo-idine)guanosine 5'-triphosphate (TNP-GTP), or the equivalent fluorescent ATP derivative (TNP-ATP).

Chemiluminescent dyes may include 5-amino-2,3-dihydro-phthalazine-1,4-dione (luminol), derivatives of iso-luminol and acridinium esters.

Any ligand may be employed for which an appropriate receptor may be found to have satisfactory specificity for the ligand. For example, the subject labeling method provides for the efficient attachment of biotin to antibodies using the subject nucleotide or nucleoside photoaffinity compounds. Specifically, this has been demonstrated by Western Blot (testing for reaction with avidin) using azido-ATP and azido-GTP compounds.

Various methods or protocols may be employed in measuring the amount of the labels. These protocols can include for example, radioimmunoassay (RIA), immunoradiometric assay (IRMA), sandwich IRMA, fluoroimmunoassay (FIA), chemiluminescent assays, bioluminescent assays, and enzyme linked immunosorbent assays (ELISA) among others.

The labeled probe of the present invention can be used in any conventional hybridization technique. Hybridization formats which may be useful in the practice of the present invention include those in which the sample is immobilized on a solid support (solid-phase hybridization) and those wherein the species are all in solution (solution hybridization). Solution hybridization is preferred in the present method. Another method of interest is the sandwich hybridization technique.

Certain factors are considered when a unique biochemical macromolecular marker is identified by means of a radioactive photoaffinity label, as is the preferred method of the present invention. For example, consideration should be given to: (a) temperature of incubation and photolysis, (b) length of incubation and photolysis, (c) concentration of photoaffinity reagent, (d) binding affinity of protein for the reagent and natural ligands, (e) stability of the photoaffinity reagent in each particular system, (f) ionic strength, pH, cofactors, (g) protein concentration, (h) intensity of photolyzing light, (i) quenching of reaction and separation of unused label, and (j) interpretation of results. Potter & Haley in Meth. in Enzymol. 91:613–633 (1983) provide a detailed account of preferred procedures for labeling a specific biochemical marker macromolecule in a sample with a photosensitive purine triphosphate azide analog.

Temperature of the photolysis reaction between the antibody sample and the selected photoaffinity label can range from 0° C. to room temperature (25° C.) or above. However, the exchange rate between bound and unbound cAMP or 8-N$_3$cAMP approaches negligible levels at 0° C., and is greatly increased at room temperature. Conversely, once 8-N$_3$cAMP is bound to the specific macromolecular marker, it may be cold trapped onto the protein by dropping the temperature to nearly 0° C. Therefore, the most preferred procedure includes preincubation of the components at room temperature, and photolysis in plates set on ice to reduce the temperature to approximately 0° to 4° C. By the present invention, the antibody containing sample is preferably incubated at room temperature with the radioactive photoaffinity probe for approximately 0.5 to 1.0 minutes. Most preferably the mixture is vortexed for 6 seconds followed by an additional 24 seconds of mixing, immediately followed by placing the sample on ice for photoactivation.

The concentration of photoaffinity reagent must be compatible with the binding affinity of the antibody which is to be labeled. Excessively high concentrations, however, can lead to undesirable nonspecific labeling which increases linearly with concentration. Best results can be obtained by experimentally determining the optimum concentration for photoincorporation. Directly related to the determination of concentration is the stability of the reagent. The stability of the reagent can be determined by thin-layer chromatography, e.g., by fluorescent cellulose thin-layer chromatography.

Ionic strength, pH, cofactor, and metal ion concentrations can each affect antibody structure, and are readily adjusted by those skilled in the art to achieve optimal labeling conditions. The higher the protein content of the sample, the denser the solution becomes to light. Therefore, in a denser solution, less UV light reaches the photoreagent per unit of time, decreasing the rate of photoincorporation. Aggregation of the protein can also affect the binding time of the reagent to the protein, thereby increasing or decreasing photoincorporation. One must experimentally redetermine optimal photolysis time when changing protein concentration if maximum incorporation of the photolabel is desired.

Detection of the labeled antibody occurs following an appropriate, predetermined incubation time to effect a reaction, and is calculated on the basis of the antibody sample and the selected photoaffinity probe.

The intensity of the photolyzing light is such that maximum photoincorporation can be obtained in a minimum amount of time without appreciable change in temperature or damage to the biological sample. Preferably the photolysis is achieved at 254 nm with an ultraviolet light source.

Ultraviolet (UV) light is essential for the activation of the photoprobe treated samples, but only a low intensity UV light is necessary. The intensity of the UV light can range from 180 to 800 µW/cm$^2$ by conventional sources to 4000 µW/cm$^2$ and above when a high intensity source is used to achieve rapid photolysis.

Photolysis times range from 15 seconds to 5 minutes and must be experimentally determined for each reaction system. For lamps having intensities of 180–800 µW/cm$^2$, the preferred photolysis time ranges from approximately 30 to 120 seconds, most preferably, photolysis is effected in approximately 30 to 60 seconds.

The distance of the light source from the sample is a determinative factor in the conditions of photolysis. A preferred method of the present invention uses an ultraviolet light source having sufficient intensity, about 6200 µW/cm$^2$, positioned at a set distance, about 1 cm from the sample, for a time sufficient to effect photoactivation, generally approximately 45 seconds.

The labeled macromolecule is typically separated from the solution containing excess unbound sample and/or label by precipitation, although other recognized methods of protein purification are possible. Recognized methods of precipitation include, but are not limited to addition of an effective protein precipitating agent, such as trichloroacetic acid (TCA), perchloric acid (PCA), acetone, ammonium sulfate polyethylene-glycol (PEG) or the like to the sample. PCA or ammonium sulfate are the preferred precipitating agents in the present method, and PCA is the particularly preferred precipitating agent.

The amount of precipitating agent is determined by the concentration of protein in the sample. The preferred concentration of the precipitating agent is that concentration which effectively precipitates the specific antibody from solution. The most preferred concentration of the precipitating agent is that mount which effectively precipitates the previously activated, photolabeled antibody sample.

The precipitating agent can be mixed with the sample as a dry batch addition or in a calculated equivalent liquid form. The required mixing time may vary with the nature of the agent selected and the size or concentration of the sample. However, the time required is that point after which essentially no additional protein is precipitated from the sample solution at the temperature selected.

The precipitated antibodies may be separated from solution by any effective means, such as centrifugation, sedimentation or filtration. A preferred method of separation of the precipitated protein from the solution is by centrifugation at a sufficient speed and for a sufficient time to effectively isolate the antibody proteins into a pellet, for example by centrifugation. However, the parameters vary with the nature of the antibody solution.

To determine the effectiveness of the precipitation and separation procedures, both the pellet and the supernatant fluid are analyzed for protein content.

The precipitated protein may be solubilized and any remaining reaction quenched by any effective, known method. The determination of the solubilizing agent would depend on the ultimate method of identifying the specific nucleotide binding protein. Therefore, such agents could include, e.g., sodium dodecyl sulfate (SDS) or urea, and certain stabilizing agents.

Any azide remaining after photolysis may be destroyed by the addition of dithiothreitol or its equivalent, and potential phosphotransfer from the triphosphate derivative N$_3$ATP or N$_3$GTP may be inhibited by chelators such as EDTA. The preferred protein solubilizing agent is a detergent, particularly SDS, most preferably in a protein solubilizing mix (PSM), such as described by Potter & Haley in *Meth. in Enzymol.*, 91:613–633 (1983) or by procedures standard to most published procedures. A particularly preferred concentration of SDS in the mix is 10%, resulting in a concentration of SDS to the final sample of 4 %.

Solubilization can occur either at 0° C. or at higher temperatures without affecting the results. However, solubilization in the present invention is effective at room temperature.

Upon solubilization, the protein sample is applied to a suitable support for separation of the protein fractions. Support materials could include, e.g., polyacrylamide gels, filter paper, starch gels or blocks, cellulose or polyurethane foam. Any effective, known method of protein separation may be used, but preferably separation is by electrophoresis over denaturing or nondenaturing gels, or over a gradient of either type. In the present method, protein separation is usually by electrophoresis on a denaturing gel.

The nature of the sample and the size of the specific nucleotide binding protein determine the concentration of the gel used, which in turn determines the time for separation and the electrical current which must be applied to best achieve protein separation. The protein fractions of the present invention most preferably may be separated by electrophoresis on an SDS-polyacrylamide gel (SDS-PAGE) or by isoelectric focusing (IEF) or on two dimensional systems (IEF×SDS-PAGE). Typically, the sample is fractionated on a 10% polyacrylamide gel, run over a period of 2½ to 3 hours, with constant amperage of 35 mA and an initial voltage of about 140 volts. Any standard electrophoresis equipment can be utilized.

The resultant gels are exposed to X-ray film and visualized by autoradiography according to methods well known in the art. The gels can also be stained to determine the presence of the unique specific protein band or to ascertain that differences in the amount of photolabel incorporation are not due to drastic changes in the protein levels. Many known protein staining methods are widely recognized, e.g., Coomassie Brilliant Blue (CBB) or silver staining. CBB is a commonly used stain that detects proteins based on a hydrophobic interaction between the proteins and the dye. Although any available staining method can be used which effectively distinguishes the specific nucleotide binding protein, CBB is the fastest and most economical for the present method.

Most preferably, each completed SDS-PAGE gel is stained with an effective amount of CBB to stain the selected protein fragments. However, many times proteins can be detected by photolabelling that cannot be detected by any protein staining procedure. In particular, the completed gel is immersed in a 10% CBB (w/v) solution for about 1 hour. Then the gel is destained in a solution to effectively remove excess stain. Particularly preferred is a destaining solution of 5% acetic acid and 10% isopropyl alcohol applied for 10–18 hours.

Finally, the specific binding protein fragments may be visualized by standard autoradiography techniques. The use of an intensifying screen effectively accelerates the visualization process of autoradiography. By the method of the present invention, the stained gel is dried, and then exposed to DuPont Cronex 4 X-ray film. The autoradiographic procedure is for variable time periods depending on the specific activity of the probe photoinserted into the proteins of each experimental sample. Alternately, if maintained at −70° C., the gel can be subjected to autoradiographic procedures while still in the gel state.

The amount of protein, as well as the radioactivity incorporated into each protein, can be quantified by known methods including, but not limited to, densitometric scans of the exposed X-ray film, or of the stained gel, or by liquid scintillation spectrometry of the protein band following excision from the gel.

As discussed supra, another application of the subject affinity labeling method comprises the attachment of desired effector molecules to antibodies, wherein these molecules are site-specifically attached to a photoaffinity site, in particular at a site or sites having high affinity for purine, azidopurine and other similar heterocyclic bases, and more particularly ATP- or GTP-analog photoaffinity compounds. This is an important application of the subject method given that the present method of attachment is site-specific and does not substantially affect the architecture of the antibody molecule or its ability to bind antigen. Therefore, effector molecule containing antibodies produced by this method will bind to a target more effectively, e.g., a tumor cell expressing the corresponding antigen Moreover, non-specific binding should be minimized which is highly significant if the antibody-effector conjugate is to be used as a therapeutic agent, since this should minimize systemic toxicity.

The subject method is applicable for site-specifically attaching any effector molecule which, when attached to a nucleotide photoaffinity compound does not adversely affect the ability of the resultant effector-nucleotide photoaffinity compound to site-specifically attach to a nucleic acid binding site comprised on the antibody molecule, or which may be site-specifically attached to a nucleotide photoaffinity compound which has been previously been site-specifically bound to a nucleic acid binding site on an antibody.

As noted previously, an effector molecule is broadly defined as any moiety which comprises a desired functions, e.g., a particular biological or chemical activity. In the preferred embodiment, the effector will comprise an activity which enables the effector-antibody conjugate to be used as a therapeutic or an imaging agent, e.g., for treating or visualizing tumors.

Examples of effector molecules within the scope of the invention include by way of example cytotoxic moteties such as enzymatically active toxins and fragments thereof such as diphtheria toxin, Pseudomonas exotoxin, ricin A, abrin A, modeccin A, alpha-sarcin, *Alevrites fordii* proteins, dianthin proteins, *Phytolacca americana* proteins (PAPI, PAPII, PAPII) , *Mornardica charantia* inhibitor, carcin, erotin, *Sapanaria officinalis* inhibitor, gelonin, mitogellin, restrictocin, phenomycin , and enomycin antitumor agents such as daunomycin, daunorubicin, methotrexate, cytokines such as interleukins (IL-1, IL-2, etc.), interferons ($\alpha$ interferon, $\beta$ interferon, $\gamma$ interferon), colony stimulating factors, tumor necrosis factors, and lymphotoxins, enzymes, radionuclides, chelating agents, growth factors, polynucleotides (DNA, RNA, antisense DNA or RNA mixtures thereof) heavy metal isotopes, as well as other moieties having therapeutic or diagnostic utility.

The effector moieties may be directly attached to the photoaffinity compound, or attachment may be effected using a bifunctional coupling agent. Examples of such reagents include by way of example SPDP, IT, dimethyl adipimidate HCl , active esters such as disuccinimidyl suberate, aldehydes such as glutaraldehyde, bis-azido compounds, bis-diazonium derivatives such as bis-(p-diazonium benzoyl)-ethylenediamine, diisocynates such as tolylene 2,6-diisocyanate, and bis-active fluorine compounds such as 1,5 -difluoro-2,4 -ditrobenzene.

Particular types of effector molecules considered to have preferred application in the invention include radiolabels and chelating agents, in particular triphosphate chelated heavy metals such as $^{111}\text{In}^{3}+$ (which has known application as a diagnostic imaging agent), nucleic acids having utility in gene therapy or antisense therapy, enzymes having diagnostic or therapeutic utility, and toxins.

Effector molecules may be attached to the photoaffinity compound, preferably a purine or azidopurine photoaffinity compound and more preferably an ATP- or GTP-analog photoaffinity compound, by various means of attachment. The selection of suitable means of attachment will depend upon the particular effector and functional groups available for covalent attachment or complexation to the particular nucleotide or nucleoside photoaffinity compound. Preferably, such chemical attachment will occur under mild conditions to preserve the activity of the antibody and effector.

For example, proteins may be attached to the subject purine or purine derivative containing photoaffinity probes, and more particularly ATP- and GTP-analog photoaffinity compounds, by converting the cis-hydroyl group on the ribose under gentle conditions to a dialdehyde. The dialdehyde will then form a Schiff's base with amino groups of proteins or other amino group containing compounds.

Also, the subject photolabeled antibodies have been shown to have very high affinity to polylysine because of the presence of a highly negatively charged triphosphate or tetraphosphate. Consequently, this will permit established procedures to be used to couple a polylysine containing polynucleotide, e.g., DNA, RNA or complexes thereof, to the photolabeled antibody. This will further enable the polynucleotide to be site-specifically targeted to an antigen expressing target, e.g., a tumor cell or a site of infection.

Additionally, it has been shown that the subject nucleotide photoaffinity compounds attach under gentle conditions to heavy metals, e.g., triphosphate chelated metals, in particular $^{111}\text{In}^{3+}$, wherein this reaction may be effected before or after the photoaffinity compound is attached to the antibody. Preferably, the photoaffinity compounds will comprise ATP- or GTP-analog photoaffinity compounds, and most preferably 2-azido-ATP, 8-azido-ATP or benzophenone-ATP. When used in vivo for therapy, the effector-antibody conjugates of the invention will be administered in therapeutically effective amounts. This will of course depend upon factors including the specific disease condition being treated, the condition of the patient, the antigen binding properties of the antibody (affinity, avidity of antibody for antigen), and the particular effector molecule that is attached to the antibody. Particular disease conditions contemplated for treatment include, e.g., cancers, infectious diseases, and genetic disorders.

The subject photoaffinity compound antibody-conjugates will normally be administered parenterally, when possible at the target, e.g., a tumor, a particular organ, or a site of infection.

For parenteral administration these conjugates will be formulated in a unit dosage injectable form (solution, suspension, emulsion) in association with a pharmaceutically acceptable parenteral vehicle. Such vehicles are inherently nontoxic, and non-therapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives. The antibody conjugates will typically be formulated in such vehicles at concentrations of about 1 mg/ml to 10 mg/ml.

The selection of an antibody subclass for therapy will depend upon the nature of the antigen. For example, an IgM may be preferred in situations where the antigen is highly specific for the target and rarely occurs on normal cells. However, where the antigen is also expressed in non-targeted, e.g., normal tissues, an IgG antibody may be preferred.

The following examples are offered to more further illustrate the nature, but are not to be construed as limiting the scope thereof.

EXAMPLES

Standard procedures and reagents were used in accordance with Maniatis et al (1982) Molecular Cloning: A Laboratory Manual, Cold Spring Harbor Laboratory, New York. Specific techniques for the photoaffinity labeling of specific nucleotide binding sites with purine phosphate azide analogues were used in accordance with Potter & Haley, Meth. in Enzymol., 90:613–633 (1983).

Example 1

Labeling Efficiency of $[\gamma^{32}P]$-8-$N_3$ ATP for SIC5 Antibody

The SIC5 antibody comprises an anti-B cell lymphoma idiotype antibody which is useful for evaluating the efficiency of labeling by idiotype solid phase assays and minor cell binding as well as in tumor imaging. Therefore, given these inherent properties, this antibody was selected to determine labeling efficiency of the subject method.

In particular, 3 μg of SIC5 antibody in 30 mL of photolysis buffer was photolyzed with increasing concentrations of $[\gamma^{32}P]$-8-$N_3$ ATP and then separated by SDS-PAGE. $^{32}P$ incorporation was detected by autoradiography and quantified by scanning on Optical Imaging Acquisition Analysis (Ambis, Inc.). Photoincorporation was quantitatively confirmed by cutting the appropriate bond and determining radioactivity by liquid scintillation counting. These results are set forth in FIG. 1. Based upon these results, it can be clearly seen that the radioactive probe is covalently attaching to both antibody heavy and light chains. It can further be seen that there is a defined saturating concentration of probe at about 200 μm for both chains. This saturation plateau provides strong evidence that there exists a unique and limited number of affinity sites of the antibody which are bound by the $[\gamma^{32}P]$-8-$N_3$ ATP compound.

Example 2

Determination of the Specificity of the Antibody Nucleic Affinity Site

In order to identify which pan of the $[\gamma^{32}P]$-8-$N_3$ ATP probe is binding the antibody, i.e., the specificity of the antibody affinity site, the following experiment was conducted.

Figure 2:
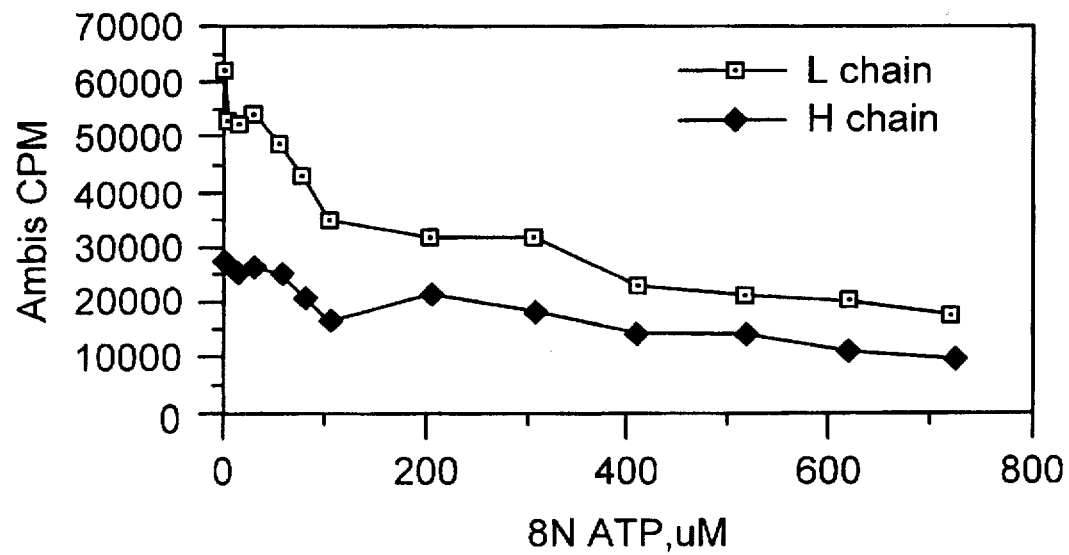
FIG. 2 is a graph which compares the photoincorporation of [γ$^{32}$P]8-N$_3$ATP into the heavy and light chain sof the SIC5 monoclonal antibody in the presence of increasing quantities of ATP wherein photoincorporation is quantified by liquid scintillation counting. The results indicate that 50% inhibition occurs at about 350 µM.

The SIC5 antibody was again labeled, but in this example labeling was performed in the presence of increasing amounts of free ATP. Specifically, 3 μg of the SIC5 antibody was photolyzed in the presence of 200 μm $[\gamma^{32}P]$-8-$N_3$ ATP using concentrations of ATP ranging from 0 to 700 μm. The labeled protein was again separated by SDS-PAGE; and radioactivity determined by liquid scintillation counting. These results are shown in FIG. 2.

Based on the results contained therein, it can be clearly seen that ATP inhibits labeling of both the heavy and light antibody chains of the SIC5 antibody. The results further indicate that 50 % of inhibition of labeling occurs at around a 350 μm ATP concentration. Thus, these results provide further evidence that the SIC5 antibody comprises one or more sites having specific affinity for the $[\gamma^{32}P]$-8-$N_3$ ATP compound.

Example 3

Labeling of the SIC5 Antibody Using $[\gamma^{32}P]$-8-$N_3$ ATP Benzophenone

Another photoactivating probe, $[^{32}P]$-8-$N_3$ ATP benzophenone, was tested to determine its efficacy for labeling the SIC5 antibody. This experiment was conducted under substantially the same conditions as Example 1, except that $[\gamma^{32}P]$-8-$N_3$ benzophenone was substituted for $[\gamma^{32}P]$-8-$N_3$. Incorporation of label into the SIC5 heavy and light chains were then measured. It was demonstrated that saturation was achieved at about 100 mM concentration of probe.

These results indicate that the SIC5 antibody comprises one or more affinity sites which are effectively labeled by the $[\gamma^{32}P]$-8-$N_3$ ATP benzophenone compound, and that the SIC5 antibody may be effectively labeled using different nucleotide photoactivating probes.

Example 4

Affinity of SIC5 Antibody Site for Oligonucleotides

Figure 3:
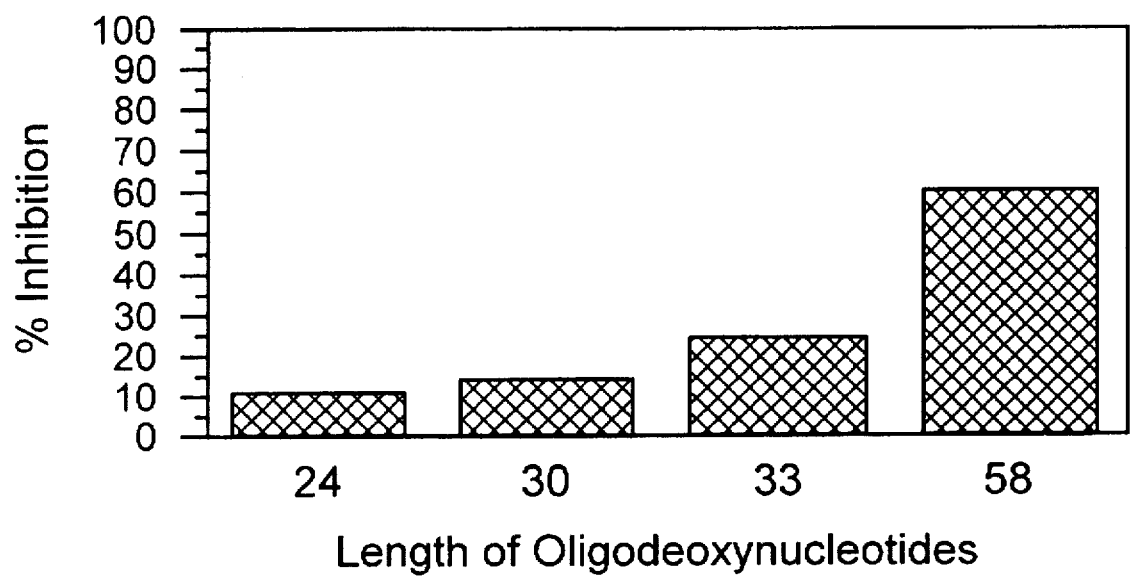
FIG. 3 is a bar graph which compares the percent inhibition of photoincorporation of [γ$^{32}$P]-8-N$_3$ATP into the SIC5 monoclonal antibody by oligonucleotides of different lengths, i.e., a 24-mer, a 30-mer, a 33-mer and a 58-mer, wherein photoincorporation is again determined by liquid scintillation counting. The bar graph shows that there is much greater inhibition with larger oligonucleotides.

The affinity of the SIC5 antibody for oligonucleotides was also evaluated using oligonucleotides of different length, to block photolabeling with an ATP probe. Specifically, 3 μg of the SIC5 antibody was incubated for two hours at 4° C. with 1 mg of a 24-mer, 30-mer, 33-mer, 58-mer, followed by incubation with 200 μm of $[\gamma^{32}P]$-8-$N_3$ ATP for 60 seconds, photolysis for 60 seconds, followed by separation of protein using SDS-PAGE. Photoincorporation was again quantitatively determined by cutting the appropriate band and determining $^{32}P$ radioactivity by liquid scintillation counting. These results are contained in FIG. 3. Based on these results, it would appear that blocking efficiency increases with the length of the oligonucleotide. This provides further evidence in support of the existence of one or more sites on the antibody having specific affinity for ATP photoaffinity probes. Additional experiments are planned using oligonucleotides of specific sequences to further analyze the sequence specificity of the affinity site(s).

Example 5

Effect of Labeling on Antigen Binding

The effect of labeling on antigen binding and antigen specificity was determined using the 3H1 anti-idiotype antibody, for which an idiotype is readily available. The binding of 3H1 to idiotype was tested in a solid phase binding assay (ELISA) using isotope labeled 3H1 in the presence of unlabeled 3H1 antibody to inhibit binding.

In particular, the idiotype antibody was used as antigen for plate coating (500 mg/well). The same mount of labeled 3H1

(3 μg) was mixed with different mounts of the unlabeled antibody and incubated for two hours at 25° C. After incubation, the wells were washed, dried, cut and $^{32}P$ radioactively counted by liquid scintillation. The 5D10 antibody was used as the non-specific cell inhibitor.

These results, using different specific mounts of unlabeled antibody ranging from 0 to 10 μg are shown in FIG. 4. It can be clearly seen from these results that the cold (unlabeled) 3H1 antibody inhibits the binding of isotope labeled 3H1.

Example 6

Cell-Surface Competition Binding of Labeled 5D10 Antibody

The binding of isotope labeled anti-B cell lymphoma idiotypic antibody to live tumor cells was tested. Specifically, $10^6$ SU-DHL-4 cells were incubated with different mounts of unlabeled antibody and the same mount of labeled antibody (3 mg/tube) for 30 minutes at 4° C. Cells were then washed using 20 % fetal calf serum (FCS) medium). Binding of $\gamma^{32}P$-labeled antibody was detected by liquid scintillation counting.

Figure 5:
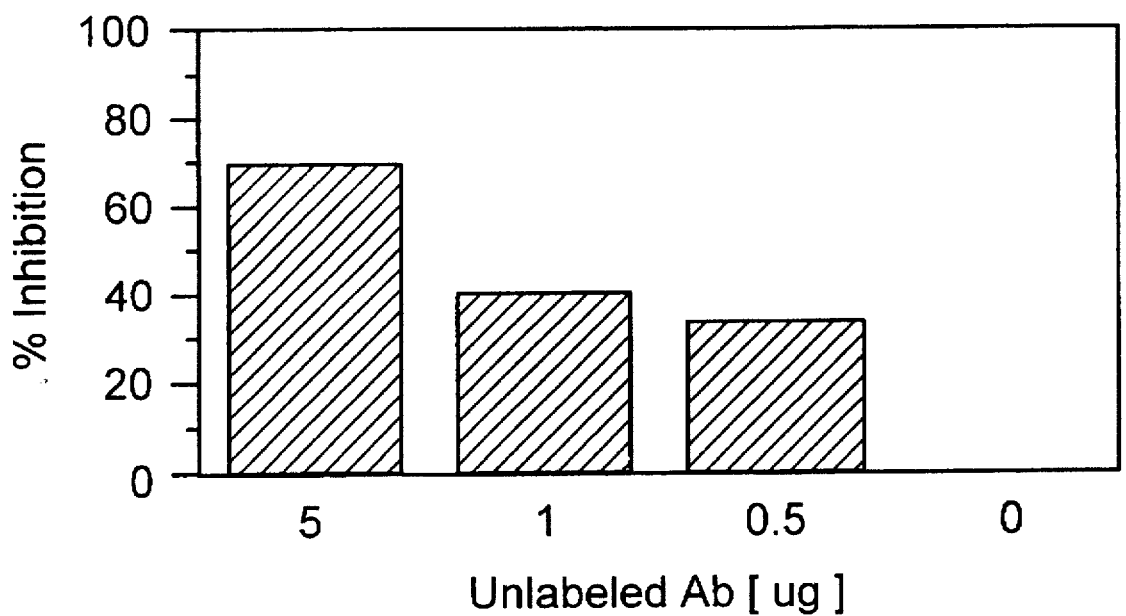
FIG. 5 is a bar graph which compares the ability of different amounts of unlabeled 5D10 monoclonal antibody (5.0, 1.0, 0.5 µg) to inhibit binding of the same amount of [γ$^{32}$P]-8-N$_3$ATP labeled 5D 10 monoclonal antibody to live DHL4 human lymphoma tumor cells.

These results are contained in FIG. 5. It can be clearly seen that the unlabeled antibody effectively inhibits binding of the isotope labeled antibody to tumor cells.

Example 7

Characterization of Labeled Antibodies by Isoelectric Focussing

Figure 6:
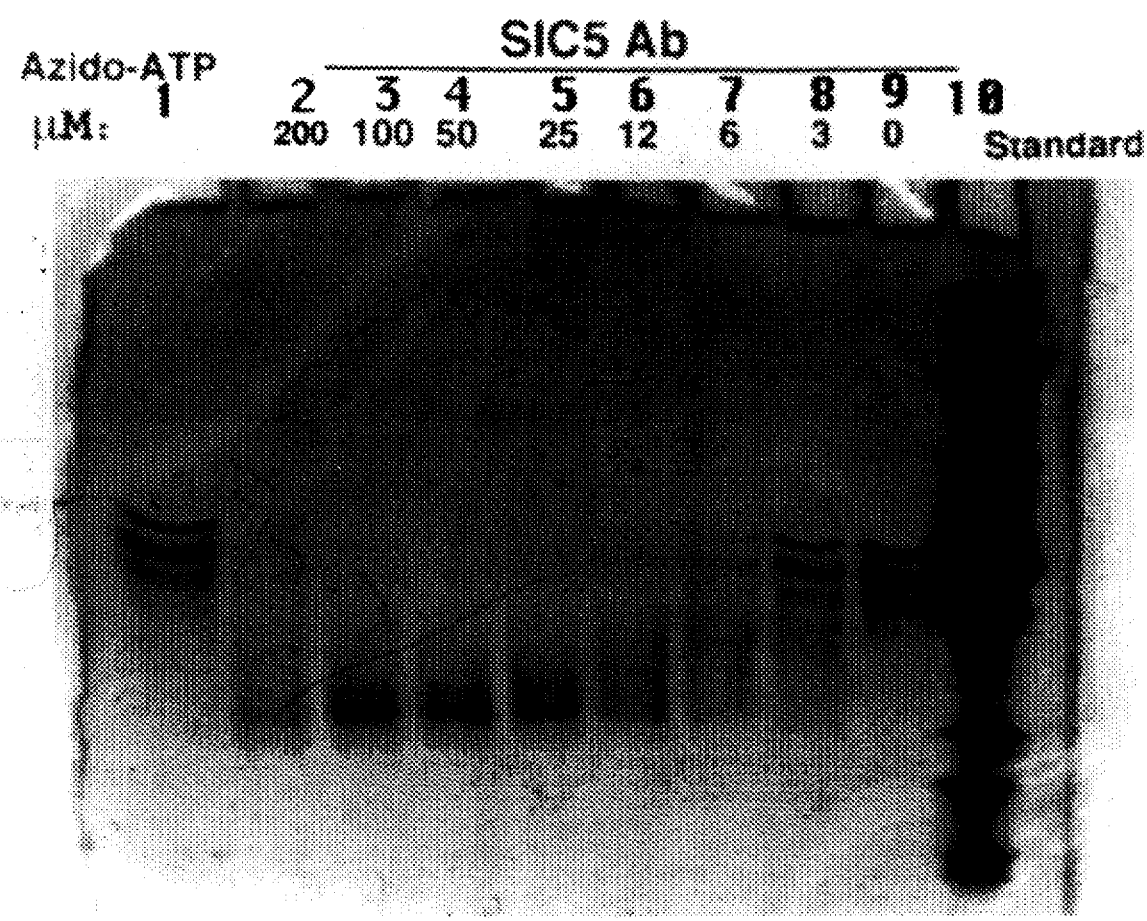
FIG. 6 is a photograph of the isoelectric focussing pattern of unlabeled and [γ$^{32}$P]-8-N$_3$ATP labeled SIC5 monoclonal antibody, wherein the SIC5 antibody is photolabeled using increasing concentrations of [γ$^{32}$P]-8-N$_3$ATP. The isoelectric focussing standards are A=cytochrome C(pI 9.6), B=equine myoglobin (pI 7.0), C=bovine carbonic anhydrase (pI 6.0), D=phycocyanin (pI 4.65) (lane 10). The unlabeled SIC5 antibody is in lane 1. The [γ$^{32}$P]-8-N$_3$ATP labelled SIC5 antibody are as follows: 3.25 µM (lane 9), 6.25 µM (lane 8), 12.5 µm (lane 7), 25µM (lane 6), 50µM (lane 5), 100 µM (lane 4), 200 µM (lane 3), 400 µM (lane 2).

Labeled antibodies were also characterized by isoelectric focusing. A representative isoelectric focusing pattern of a labeled and unlabeled antibody is found in FIG. 6.

Isoelectric focusing was effected at a pH ranging from 3 to 10 using SIC5 antibodies which had been photolabeled with increasing concentrations of $[\gamma^{32}P]$-8-$N_3$ ATP. The isoelectric focusing standards used were:

A=cytochrome C (pI 9.6), B=equine myoglobin (pI 7.0), C=bovine carbonic anhydrase (pI 6.0), D =phycocyanin (pI 4.65) (lane 10).

The unlabeled antibody is shown in lane 1.

SIC5 antibody (5 μg) was photolyzed by 3.125 μm (lane 9), 6.25 μm (lane 8), 12.5 μm (lane 7), 25 μm (lane 6), 50 μm (lane 5), 100 μm (lane 4), 200 μm (lane 3), and 400 μm (lane 2) $[\gamma^{32}P]$-8-$N_3$ ATP.

Example 8

Figure 7:
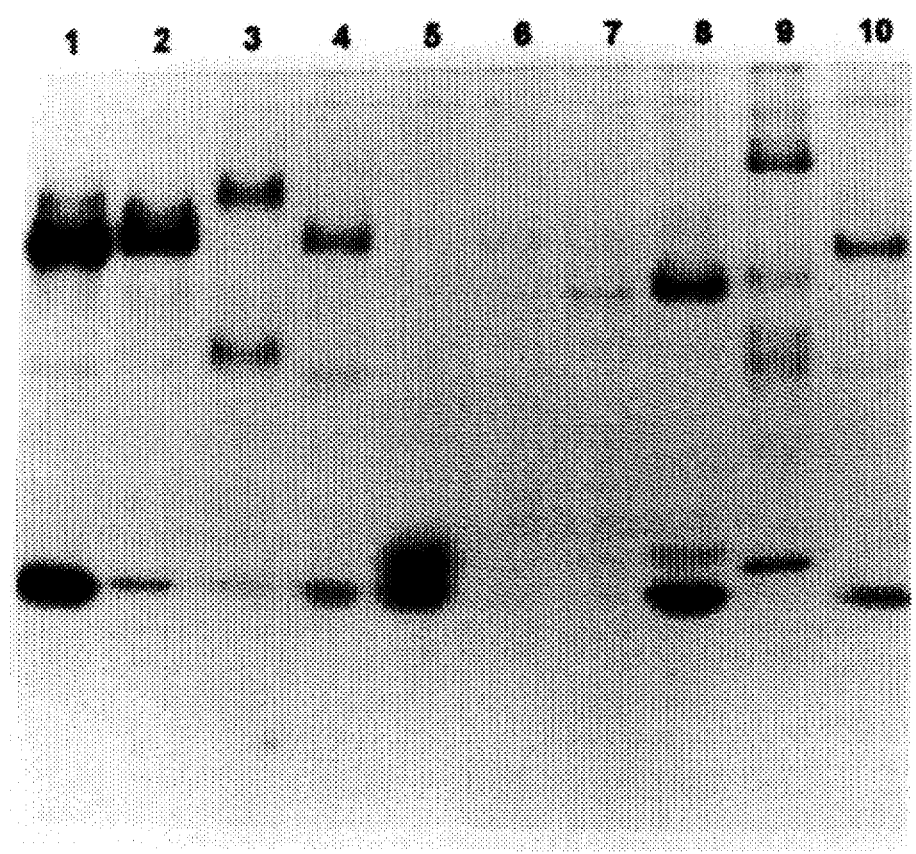
FIG. 7 is a photograph of an autoradiograph made from an SDS-PAGE on which different antibodies which had been photolabeled with [γ$^{32}$P]-8-N$_3$ATP were separated. In particular, autoradiograph shows separation of a murine monoclonal IgG1 antibody, 5D10 monoclonal antibody (lane 1), murine myeloma IgG1 (lane 2), murine myeloma IgA (lane 3), goat Ig (lane 4), goat (Fab)$_2$ fragments (lane 5), human myeloma IgG1K (lane 6), human myeloma IgG1 (lane 7), human myeloma IgM (lane 8), murine monoclonal IgM (lane 9) and murine monoclonal IgG2b, SIC5 (lane 10) which had photolyzed in the presence of 200 µM [γ$^{32}$P]-8-N$_3$ATP and were separated by 8–16% gradient SDS-PAGE, stained with Coomassive Blue, dried and autoradiographed.

Labeling, of Antibodies of Different Species and Isotype Using $[\gamma^{32}P]$-8-$N_3$ ATP In this experiment, antibodies of different species, origin and isotype were labeled with $[\gamma^{32}P]$-8-$N_3$ ATP. Specifically, murine, goat, human and rabbit antibodies were labeled with $[\gamma^{32}P]$-8-$N_3$ ATP. Labeling was again effected substantially in accordance with Example 1. The same amount (3 μg) of the respective antibodies [murine monoclonal IgG1, 5D10 (lane 1), murine myeloma IgG1 (lane 2), murine myeloma IgA (lane 3), goat Ig (lane 4), goat (Fab)$_2$ fragments (lane 5), human myeloma IgG1 K (lane 6), human myeloma IgG1 1 (lane 7), human myeloma IgM (lane 8), murine monoclonal IgM (lane 9), murine monoclonal IgG2b, SIC5 (lane 10)] was photolyzed in the presence of 200 μm $[\gamma^{32}P]$-8-$N_3$ ATP and separated by 8–16% gradient SDS-PAGE. Following electrophoresis, the gel was stained with Coomassie Blue, dried and autoradiographed. These results are contained in FIG. 7.

The results indicate that these different antibodies effectively incorporate the label into the heavy and light chains and that the amount of incorporation varies with the different antibodies. It can further be seen that a Fab fragment (goat Ig is Fab fragment) is effective labeled.

Thus, these results indicate that nucleotide affinity binding sites suitable for photoaffinity nucleotide labeling are comprised on antibodies of different species, origin and an antibody of different isotype. Moreover, these results indicate that antibody fragments, as well as intact antibodies may be effectively labeled using nucleotide photoaffinity probes.

While the invention has been described in the terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A nucleotide photoaffinity compound-antibody conjugate produced by reacting an antibody-containing sample with an effective amount of a nucleotide photoaffinity compound under conditions which provide for the site-specific photoinsertion of said nucleotide photo-affinity compound at one or more nucleotide binding sites in the antibody contained in the sample.

2. The nucleotide photoaffinity compound-antibody conjugate of claim 1, wherein said nucleotide photoaffinity compound is an ATP- or GTP-analog photoaffinity compound.

3. The nucleotide photoaffinity compound-antibody conjugate of claim 1, wherein the nucleotide photoaffinity compound site-specifically attaches to one or more sites having high affinity for purine, azidopurine or heterocyclic bases having a similar structure to purine.

4. The nucleotide photoaffinity compound-antibody conjugate of claim 2, wherein the ATP- or GTP-analog is selected from the group consisting of 2-azido-ATP, 8-azido-ATP and benzoylphenone-ATP.

5. The nucleotide photoaffinity compound-antibody conjugate of claim 1, wherein said antibody is selected from the group consisting of polyclonal antibodies, monoclonal antibodies, recombinant antibodies, chimeric antibodies, bispecific antibodies and fragments thereof.

6. The nucleotide photoaffinity compound-antibody conjugate of claim 1, wherein the nucleotide photoaffinity compound is covalently bound or complexed to a reporter.

7. The nucleotide photoaffinity compound-antibody conjugate of claim 6, wherein the reporter is selected from the group consisting of radiolabels, enzymes, chromophores, polynucleotides, and fluorochromes.

8. The nucleotide photoaffinity compound-antibody conjugate of claim 6, wherein the reporter is a radiolabel.

9. The nucleotide photoaffinity compound-antibody conjugate of claim 1, wherein site-specific photoinsertion is effected using ultraviolet light.

10. The nucleotide photoaffinity compound-antibody conjugate of claim 1, wherein the nucleotide photoaffinity compound is covalently bound to or complexed to an effector molecule.

11. The nucleotide photoaffinity compound-antibody conjugate of claim 10, wherein the effector is selected from the group consisting of proteins DNA, RNA, DNA or RNA containing complexes toxins, cytokines, chelatin agents, and radiolabels.

12. The nucleotide photoaffinity compound-antibody conjugate of claim 10, wherein the effector is a heavy metal.

13. The nucleotide photoaffinity compound-antibody conjugate of claim 12, wherein the heavy metal is radioactive.

14. The nucleotide photoaffinity compound-antibody conjugate of claim 12, wherein the heavy metal is iron or mercury.

15. The nucleotide photoaffinity compound-antibody conjugate of claim 13, wherein the radioactive heavy metal is $^{111}In^{3+}$.

* * * * *